(12) United States Patent
Kamachi et al.

(10) Patent No.: US 7,261,961 B2
(45) Date of Patent: Aug. 28, 2007

(54) THERMOELECTRIC CONVERSION APPARATUS

(75) Inventors: Atsushi Kamachi, Utsunomiya (JP); Hitoshi Okanobori, Utsunomiya (JP); Shunsuke Itami, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 563 days.

(21) Appl. No.: 10/807,723

(22) Filed: Mar. 23, 2004

(65) Prior Publication Data

US 2004/0191592 A1    Sep. 30, 2004

(30) Foreign Application Priority Data

Mar. 25, 2003    (JP)    ............... 2003-083238

(51) Int. Cl.
*H01M 8/06*    (2006.01)
*H01M 8/18*    (2006.01)

(52) U.S. Cl. .............................. 429/20; 429/17; 429/26

(58) Field of Classification Search ..................... None
See application file for complete search history.

(56) References Cited

U.S. PATENT DOCUMENTS 5,798,187 A * 8/1998 Wilson et al. ................ 429/26
6,127,054 A   10/2000 Ando et al.

FOREIGN PATENT DOCUMENTS

JP    58044671    3/1983
JP    61072995    4/1986
JP    2002-208430    7/2002

OTHER PUBLICATIONS

Ando Y. et al: "Proposal and fundamental analysis of thermally regenerative fuel cell utilizing solar heat", IECEC '97. Proceedings of the 32nd Intersociety Energy Conversion Engineering Conference. Energy Systems, Renewable Energy Resources, Environmental Impact and Policy Impacts on Energy. Honolulu, HI Jul. 27-Aug. 1, 1997, Intersociety Energy Convers, vol. 3 & 4, Jul. 27, 1997, pp. 1860-1864, XP010268861 ISBN: 0-7803-4515-0, point "thermally regenerative fuel cell".

* cited by examiner

*Primary Examiner*—Jonathan Crepeau
(74) *Attorney, Agent, or Firm*—Lahive & Cockfield, LLP; Anthony A. Laurentano, Esq.

(57) ABSTRACT

A thermoelectric conversion apparatus having a high thermoelectric conversion efficiency comprises: a dehydrogenation reactor for generating hydrogen and acetone by an endothermic dehydrogenation reaction of isopropyl alcohol in the presence of a dehydrogenation catalyst and heat from a heat source, and a fuel cell which generates electricity by an electrochemical reaction of the hydrogen and the acetone produced by the dehydrogenation reactor. A module is constructed by integrating the dehydrogenation reactor and an electricity generating layer constituting the fuel cell into a stack.

3 Claims, 9 Drawing Sheets

THERMOELECTRIC CONVERSION APPARATUS

Priority is claimed to Japanese Patent Application No. 2003-83238, filed Mar. 25, 2003, which are incorporated herein by reference.

BACKGROUND OF THE INVENTION

1. Field of the Invention

This invention relates to a thermoelectric conversion apparatus, which converts thermal energy to electrical energy.

2. Description of Related Art

In recent years, attention has been given to thermoelectric conversion systems containing heat regenerative type fuel cells as thermoelectric conversion apparatuses that recover heat at comparatively low temperatures (referred to hereunder as low grade heat), up to approximately 100° C. for example, and convert it to electrical energy (refer to patent reference 1 and patent reference 2).

In these thermoelectric conversion systems, thermal energy is supplied to induce an endothermic dehydrogenation reaction in a particular type of organic compound on a catalyst, and hydrogen and dehydrogenated substances (referred to hereunder as dehydrogenated substances), which are produced by this reaction, and hydrogen are reacted (hydrogenation reaction) electro-chemically to recover electrical energy. In such a thermoelectric conversion system, since there is no thermodynamic restriction (Carnot efficiency), a highthermoelectric conversion efficiency can be expected.

For example, in a case where acetone, being a dehydrogenated substance, undergoes a hydrogenation reaction to create isopropyl alcohol (abbreviated hereunder as IPA), its reaction equation is represented as equation (1)

$$(CH_3)_2CO \rightarrow H_2 + (CH_3)_2CHOH \qquad (1)$$

Here, when the operating temperature is 25° C., the value of the enthalpy variation $\Delta H = -55.5$ kJ/mol, and the Gibbs free energy variation $\Delta G = 27.5$ kJ/mol. Therefore, the thermoelectric conversion efficiency $\eta$ is $\eta = \Delta G/\Delta H = 49.5\%$.

Patent Reference 1: Japanese Patent No. 1-25972.
Patent Reference 2: Japanese Unexamined Patent Application, First Publication No. 2002-208430.

In actual usage, considering for example the temperature of waste heat to be applied as thermal energy to induce an endothermic dehydrogenation reaction, or the activation temperature of a catalyst to induce an endothermic dehydrogenation reaction, it is necessary to operate at around 100° C. However, in the case where the operating temperature is 100° C., since the value of the enthalpy variation $\Delta H = -56.4$ kJ/mol, and the Gibbs free energy variation $\Delta G = 12.2$ kJ/mol, the thermoelectric conversion efficiency $\eta$ is $\eta = \Delta G/\Delta = 21.6\%$, which is lower than the 100° C. Cannot efficiency (29.8%).

SUMMARY OF THE INVENTION

Therefore, the present invention is to provide a thermoelectric conversion apparatus that can obtain high thermoelectric conversion efficiency by using heat generated by a hydrogenation reaction as a heat source for an endothermic dehydrogenation reaction.

In order to solve the above-described problem, a first aspect of the invention is a thermoelectric conversion apparatus (for example, a thermoelectric conversion apparatus 100 in the embodiments described later), comprising: a dehydrogenation reactor (for example dehydrogenation reactor 4 in the embodiments described later) which induces an endothermic dehydrogenation reaction in an organic compound (for example, isopropyl alcohol in the embodiments described later) in the presence of a dehydrogenation catalyst and heat from a heat source (for example, main fuel cell 2 in the embodiments described later), and generates hydrogen and a dehydrogenated substance (for example, acetone in the embodiments described later); and a fuel cell (for example, sub fuel cell 5 in the embodiments described later) which generates electricity by an electrochemical reaction of the hydrogen and the dehydrogenated substance produced by the dehydrogenation reactor, wherein self-generated heat when the fuel cell operates is supplied to the dehydrogenation reactor in addition to the heat from the heat source.

If the thermoelectric conversion efficiency when self-generated heat is not utilized is $\eta G$, and the fuel heat utilization factor when the heat generated by the fuel cell is utilized for a dehydrogenation reaction in the dehydrogenation reactor is $\eta H$, the thermoelectric conversion efficiency $\eta$ in the case where the self-generated heat is utilized is expressed by the following equation.

$$\eta = \eta G \cdot \eta H / \{1 - \eta H (1 - \eta G)\}$$

Accordingly, in a construction as above, it is possible to increase the thermoelectric conversion efficiency of a thermoelectric conversion apparatus more significantly than in the case where the self-generated heat is not utilized.

A second aspect of the invention is that there is provided: a dehydrogenation reactor (for example dehydrogenation reactor 4 in the embodiments described later) which induces an endothermic dehydrogenation reaction in an organic compound (for example, isopropyl alcohol in the embodiments described later) in the presence of a dehydrogenation catalyst and heat from a heat source (for example, main fuel cell 2 in the embodiments described later), and generates hydrogen and a dehydrogenated substance (for example, acetone in the embodiments described later); and a fuel cell (for example, sub fuel cell 5 in the embodiments described later) which generates electricity by an electrochemical reaction of the hydrogen and the dehydrogenated substance produced by the dehydrogenation reactor, wherein the dehydrogenation reactor (for example, module 30 in the embodiments described later) and the fuel cell (for example, electricity generating layer 20 in the embodiments described later) are integrated in a stack.

Using such a construction, it is possible to transfer self-generated heat directly from a fuel cell to a dehydrogenation reactor, thus enabling heat loss to be reduced dramatically. Also, it is possible to increase the thermoelectric conversion efficiency of a thermoelectric conversion apparatus considerably.

A third aspect of the invention is that in the second aspect of the invention, the dehydrogenation reactor is constructed by stacking catalyst layers (for example, catalyst layers 40 in the embodiments described later) containing a dehydrogenation catalyst, and a supply and discharge layer (for example, supply and discharge layer 50 in the embodiments described later) comprising a supply path (for example, IPA supply path 54 in the embodiments described later) for supplying an organic compound to the catalyst layers and a discharge path (for example, hydrogen-acetone discharge path 55 in the embodiments described later) for discharging hydrogen and a dehydrogenated substance, which are produced in the catalyst layers, wherein electricity generating layers (for example, electricity generating layers 20 in the embodiments described later) of the fuel cell are placed in contact with the catalyst layer.

Using such a construction, it is possible to supply an organic compound from the supply path of the supply and discharge layer to the dehydrogenation catalyst of the catalyst layers, and it is possible to discharge hydrogen and a dehydrogenated substance, which are produced by an endothermic dehydrogenation reaction in the dehydrogenation catalyst, to the discharge path of the supply and discharge layer. Since it is possible to construct a dehydrogenation reactor by simply stacking catalyst layers, and arranging a supply and discharge layer and an electricity generating layer of the fuel cell so as to be in contact with the catalyst layers, it is possible to transfer the self-generated heat from the fuel cell reliably, the fuel heat utilization factor can be increased, and it is possible to increase the dehydrogenation reaction efficiency of the dehydrogenation reactor. Moreover, by increasing the number of stacked layers, it is possible to construct a small-sized, but high performance, dehydrogenation reactor, thus enabling a stacked dehydrogenation reactor and fuel cell to be physically small.

A fourth aspect of the invention is that in the third aspect of the invention, the dehydrogenation catalyst and the generating surface of the electricity generating layer are arranged so as to align when stacked.

Using such a construction, it is possible to further increase the fuel heat utilization factor of the self heating due to the power generation of the fuel cell.

A fifth aspect of the invention is that in the third and the fourth aspects of the invention, catalyst layers are stacked on both sides of the supply and discharge layer, and an organic compound, hydrogen and a dehydrogenated substance are supplied and discharged between the supply and discharge layer and the catalyst layers on both sides.

Using such a construction, it is possible to transfer heat from both surfaces of the supply and discharge layer to the catalyst layers, thus enabling a thermoelectric conversion apparatus with high processing performance to be made smaller and thinner.

A sixth aspect of the invention is that in any one of the third aspect through the fifth aspect of the invention, the catalyst layer and the electricity generating layer are each formed from a metal substrate (for example, separators 22 and 23, and substrates 51, 52 and 53 in the embodiments described later).

Using such a construction, the heat transfer properties of self-generated heat from a electricity generating layer are improved.

A seventh aspect of the invention is that there is provided: a dehydrogenation reactor (for example, dehydrogenation reactor 4 in the embodiments described later) which induces an endothermic dehydrogenation reaction in an organic compound (for example, isopropyl alcohol in the embodiments described later) in the presence of a dehydrogenation catalyst and heat from a heat source (for example, main fuel cell 2 in the embodiments described later), and generates hydrogen and a dehydrogenated substance (for example, acetone in the embodiments described later); and a fuel cell (for example, sub fuel cell 5 in the embodiments described later) which generates electricity by an electrochemical reaction of the hydrogen and the dehydrogenated substance produced by the dehydrogenation reactor, and there is provided a heating medium circulating path (for example, a cooling water circulating circuit 15 in the embodiments described later) which circulates a heating medium between the dehydrogenation reactor and the fuel cell.

Using such a construction, it is possible to supply self-generated heat of the fuel cell to the dehydrogenation reactor via the heating medium, and it is possible to increase the thermoelectric conversion efficiency of a thermoelectric conversion apparatus considerably. Furthermore, it is possible to make the dehydrogenation reactor and the fuel cell different entities. Thus the flexibility in the shape and size of a thermoelectric conversion apparatus, and the flexibility in its layout, are increased, and it is possible to control the temperatures of a fuel cell and a dehydrogenation reactor individually using the heating medium.

DETAILED DESCRIPTION OF THE INVENTION

Hereunder is a description of embodiments of a thermoelectric conversion apparatus according to the present invention with reference to the drawings of FIG. 1 to FIG. 10. All of the following embodiments are modes for incorporating in fuel cell automobiles.

Embodiment 1

At first is a description of a first embodiment of a thermoelectric conversion apparatus according to the present invention will be described with reference to the drawings of FIG. 1 to FIG. 8.

Figure 1:
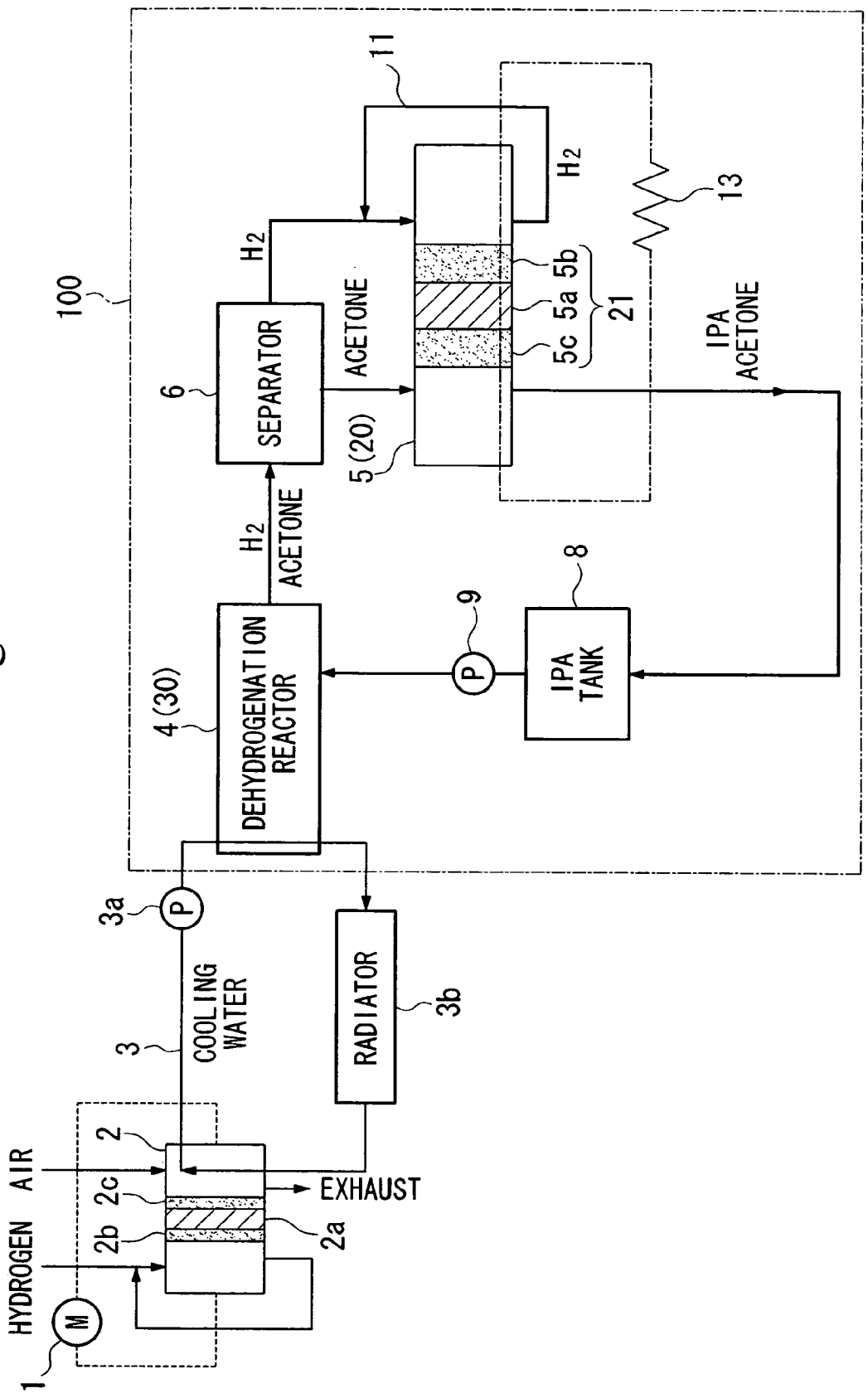
FIG. 1 is a schematic structural diagram of a vehicle fuel cell system incorporating a thermoelectric conversion apparatus of a first embodiment according to the present invention.

FIG. 1 is a schematic structural diagram of a vehicle fuel cell system incorporating a thermoelectric conversion apparatus of the first embodiment. A main fuel cell 2 for supplying power to a drive motor 1 is a fuel cell using hydrogen and oxygen as reaction gasses. It is constructed by stacking a plurality of cells of a membrane structure in which a solid polymer electrolyte membrane 2a is sandwiched between an anode electrode 2b and a cathode electrode 2c (only a single cell unit is shown in FIG. 1), and electricity is generated by supplying hydrogen to the anode side, and supplying air to the cathode side. This main fuel cell 2 is provided with a cooling water circulating circuit 3 for circulating cooling water to cool the main fuel cell 2, and a cooling water pump 3a and an air cooling type radiator 3b are provided in the cooling water circulating circuit 3.

Furthermore, a part of the cooling water circulating circuit 3 is incorporated within a dehydrogenation reactor 4, which is a part of a thermoelectric conversion apparatus 100, and cooling water passes through the main fuel cell (heat source) 2, the dehydrogenation reactor 4, and the radiator 3b, in that order. The cooling water heated by the fuel cell 2 is cooled by thermal exchange inside the dehydrogenation reactor 4, cooled afterwards by thermal exchange inside the radiator 3b, and then returned to the main fuel cell 2.

The thermoelectric conversion apparatus 100 comprises the dehydrogenation reactor 4, a sub fuel cell 5, a separator 6, and an IPA tank 8 as its main components, and is constructed by connecting them in a closed circuit. The IPA (isopropyl alcohol), being an organic compound to be dehydrogenated, is stored in the IPA tank 8, and is supplied to the dehydrogenation reactor 4 by an IPA pump 9.

The dehydrogenation reactor 4 is a catalytic reactor containing a dehydrogenation catalyst to induce a dehydrogenation reaction, and causes the IPA to undergo an endothermic dehydrogenation reaction in the presence of the dehydrogenation catalyst and heat of the main fuel cell 2, to generate hydrogen and acetone (dehydrogenated substance). In order to perform this endothermic dehydrogenation reaction efficiently, the heat of the sub fuel cell 5, which is a part of the thermoelectric conversion apparatus 100, is supplied to the dehydrogenation reactor 4 in addition to the heat of the main fuel cell 2.

In the dehydrogenation reactor 4, the hydrogen and acetone, produced by the dehydrogenation reaction, are discharged from the dehydrogenation reactor 4 as a mixed gas and supplied to the separator 6. The separator 6 separates the hydrogen from the acetone, and is provided with a hydrogen separating film, for example. The hydrogen separated by the separator 6 is supplied to the anode side of the sub fuel cell 5, and the acetone is supplied to the cathode side.

The sub fuel cell 5 is constructed by stacking a plurality of electricity generating layers 20 (FIG. 1 shows only one electricity generating layer) of a membrane structure (abbreviated hereunder as MEA) in which a solid polymer electrolyte membrane 5a is sandwiched between an anode electrode 5b and a cathode electrode 5c, and when hydrogen is supplied to the anode side, and acetone is supplied to the cathode side, the hydrogen is ionized in the catalyst on the anode electrode 5b, and electrons flow in an outer circuit 13 to generate electricity. On the other hand, hydrogen ions pass through the solid polymer electrolyte membrane 5a and are transferred to the cathode electrode 5c, the acetone combines with protons and electrons, and an exothermic hydrogenation reaction occurs on the acetone, which generates IPA. That is, this sub fuel cell 5 generates electricity by supplying the hydrogen and acetone produced in the dehydrogenation reactor 4 to the anode and the cathode respectively, inducing an electrochemical reaction. Afterwards, the electricity generated in the sub fuel cell 5 is utilized in electric vehicle equipment.

Unreacted hydrogen, which is discharged from the anode side of the sub fuel cell 5, is returned to the anode side of the sub fuel cell 5 via a hydrogen circuit 11, and used for circulation. On the other hand, the IPA and unreacted acetone, which are produced in the acetone hydrogenation reaction, are discharged from the cathode side of the sub fuel cell 5 and returned to the IPA tank 8 to be used for circulation.

In the case where the catalyst of the anode electrode 5b of the sub fuel cell 5 is inactive to acetone (for example, palladium (Pd)), the separator 6 is unnecessary. In that case, the mixed gas of hydrogen and acetone, discharged from the dehydrogenation reactor 4, may be supplied to both the anode side and cathode side of the sub fuel cell 5. In this manner, it is also possible to generate electricity in the sub fuel cell 5. Furthermore, the arrangement may also be such that the IPA and acetone discharged from the cathode side of the sub fuel cell 5 are separated, and only the separated IPA is returned to the IPA tank 8, while the acetone is returned to the cathode side of the sub fuel cell 5.

Figure 2:
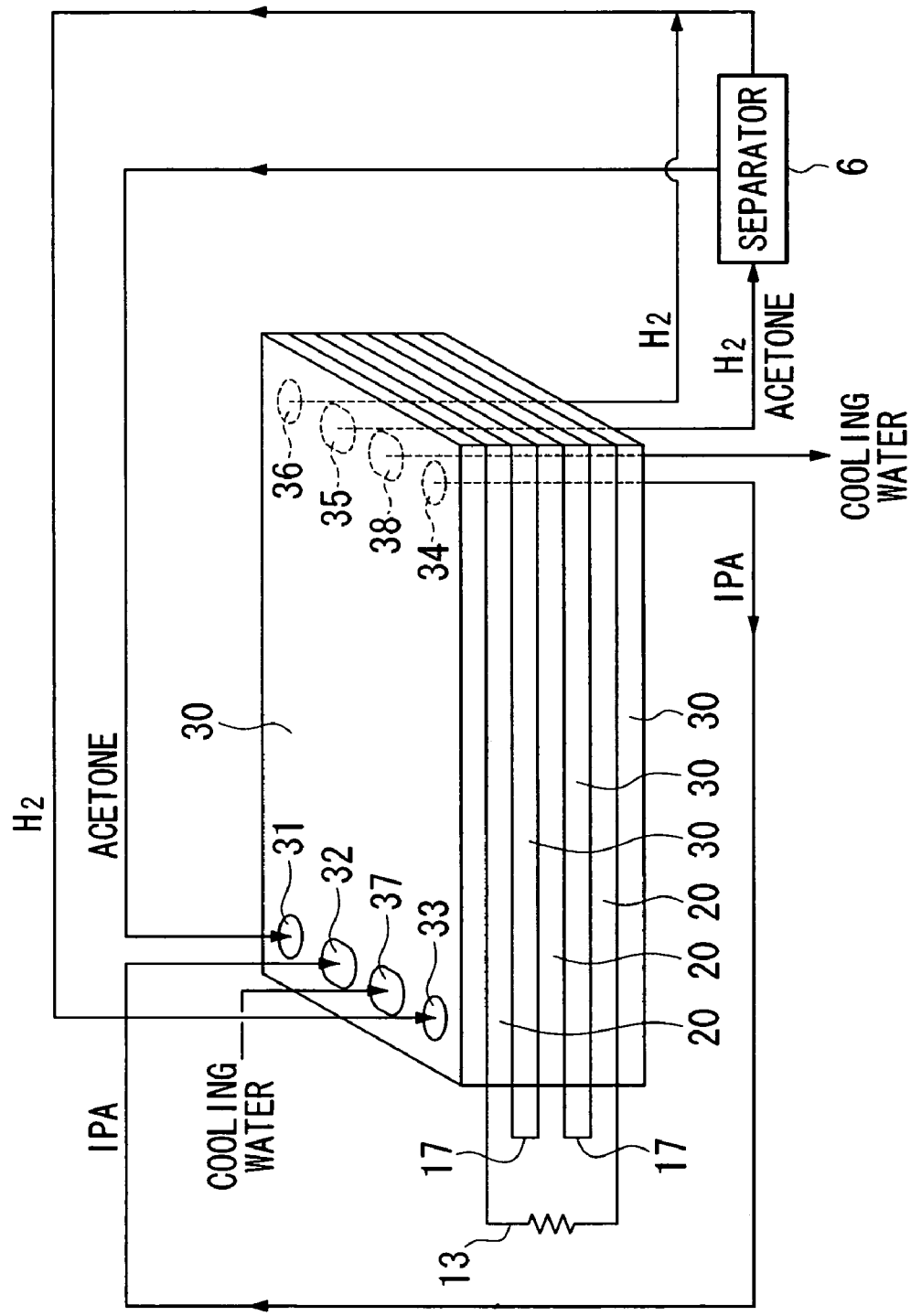
FIG. 2 is a schematic diagram showing an example of a case where a dehydrogenation reactor and a sub fuel cell in the first embodiment of the thermoelectric conversion apparatus according to the present invention are integrated.

Incidentally, in this thermoelectric conversion apparatus 100, heat generated when the sub fuel cell 5 generates electricity is absorbed by the dehydrogenation reactor 4 as described previously. However, especially in the first embodiment, as shown in FIG. 2, the electricity generating layers 20, being component pairs of the sub fuel cell 5, and reactor modules (referred to hereunder as modules) 30, being composite units of the dehydrogenation reactor 4, are stacked alternately to integrate the dehydrogenation reactor 4 and the sub fuel cell 5, so that heat generated by the electricity generating layers 20 is transferred to the adjacent modules 30 directly. In FIG. 2, reference symbol 17 denotes interconnect lines for electrically connecting the electricity generating layers 20 in series.

Here, heat from the sub fuel cell 5 is self-generated by the thermoelectric conversion apparatus 100 formed by the closed circuit containing the dehydrogenation reactor 4 and the sub fuel cell 5, and this self-generated heat is supplied to the dehydrogenation reactor 4.

If the thermoelectric conversion efficiency when self-generated heat is not utilized is $\eta G$, and the fuel heat utilization factor when the heat generated by the sub fuel cell 5 is utilized for the dehydrogenation reaction is $\eta H$, thethermoelectric conversion efficiency $\eta$ in the case where self-generated heat is utilized is expressed by the following equation.

$$\eta = \eta G \cdot \eta H / \{1 - \eta H (1 - \eta G)\}$$

Accordingly, if the self-generated heat is utilized for the dehydrogenation reaction, it is possible to increase the thermoelectric conversion efficiency. For example, in the case where the operating temperature of the dehydrogenation reactor 4 is 100° C., the thermoelectric conversion efficiency $\eta G$ when self-generated heat is not utilized is 21.6%, whereas the thermoelectric conversion efficiency $\eta$ in the case where self-generated heat is utilized, and the fuel heat utilization factor $\eta H$ is 90%, is 66%, which is an improvement of approximately three times, which greatly exceeds the Carnot efficiency (29.8%).

Next is a description of the structures of the sub fuel cell 5 and the dehydrogenation reactor 4 of the first embodiment.

Figure 3:
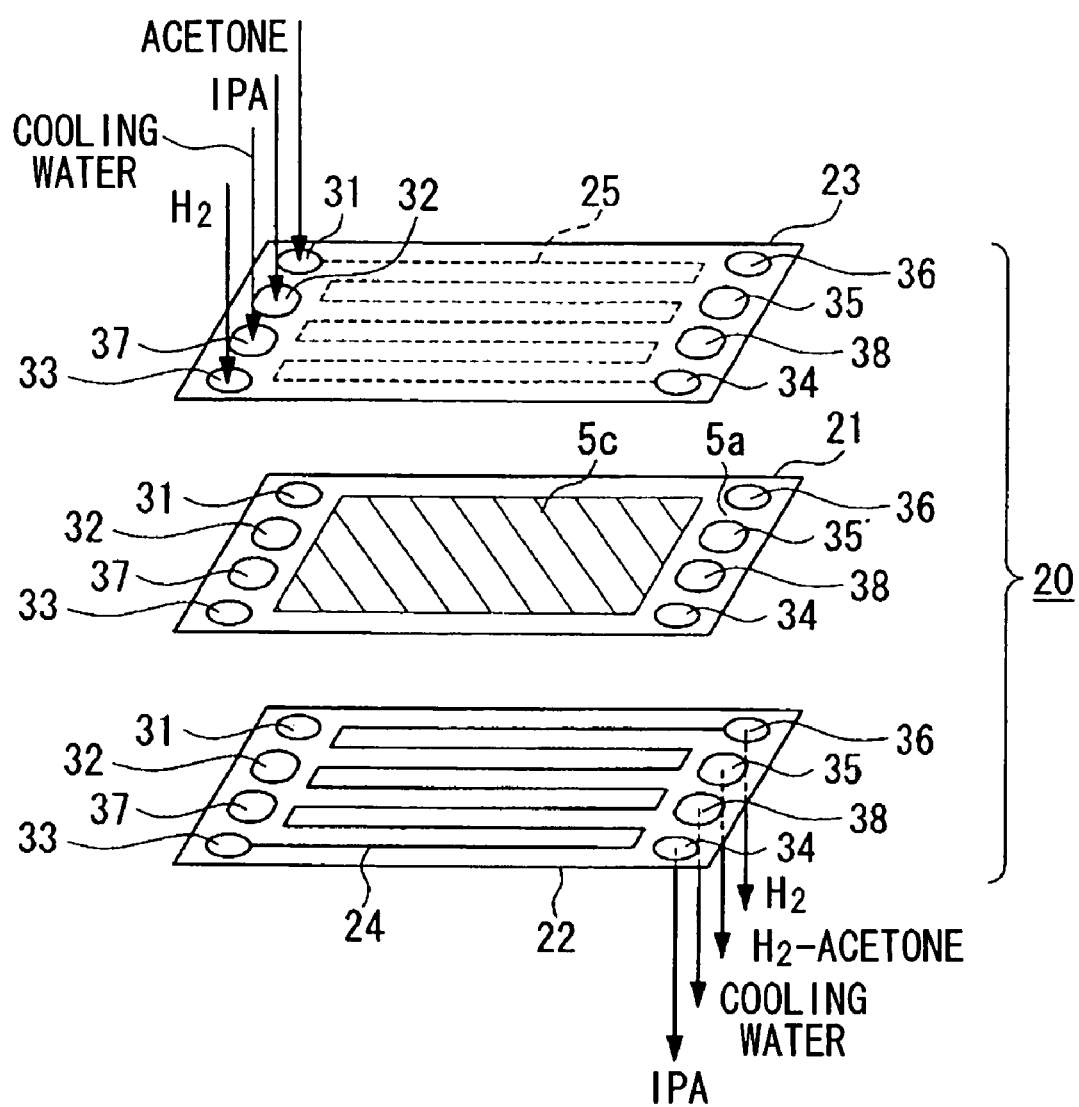
FIG. 3 is an exploded perspective view of an electricity generating layer constituting the sub fuel cell in the first embodiment.

FIG. 3 is an exploded perspective view of the sub fuel cell 5. A electricity generating layer 20 is formed as a rectangular sheet, and constructed by stacking metal separators 22 and 23, such as stainless steel or the like, on both sides of an MEA 21. Acetone supply holes 31, IPA supply holes 32, hydrogen supply holes 33, and refrigerant supply holes 37, for supplying refrigerant to the main fuel cell 2 to receive heat from the main fuel cell (heat source), are arranged along the short side of the electricity generating layers 20, passing through in the laminated direction, and acetone discharge holes 34 for exhausting acetone and IPA produced by the fuel cell reaction of the sub fuel cell 5, hydrogen-acetone discharge holes 35 for exhausting hydrogen and acetone produced by inducing a dehydrogenation reaction in IPA, hydrogen discharge holes 36 for exhausting unused hydrogen that has not contributed to the fuel cell reaction of the sub fuel cell 5, and refrigerant discharge holes 38 for exhausting refrigerant that has transferred heat to the dehydrogenation reactor 4 and cooled, are arranged along the other short side of the electricity generating layers 20, passing through in the laminated direction. The acetone supply holes 31 and the acetone discharge holes 34 are arranged on one diagonal of the electricity generating layers 20, and the hydrogen supply holes 33 and the hydrogen discharge holes 36 are arranged on the other diagonal of the electricity generating layers 20. The IPA supply holes 32 and the refrigerant supply holes 37 are arranged between the acetone supply holes 31 and the hydrogen supply holes 33, and the hydrogen-acetone discharge holes 35 and the refrigerant discharge holes 38 are arranged between the acetone discharge holes 34 and the hydrogen discharge holes 36.

A predetermined region in the central part of a solid polymer electrolyte membrane 5a of the MEA 21 is formed as a sandwich between an anode electrode 5b and a cathode electrode 5c. The acetone supply hole 31, the IPA supply hole 32, the hydrogen supply hole 33, the acetone discharge hole 34, the hydrogen-acetone discharge hole 35, the hydrogen discharge hole 36, the refrigerant supply hole 37, and the refrigerant discharge hole 38 are located outside the anode electrode 5b and the cathode electrode 5c in the solid polymer electrolyte membrane 5a. In FIG. 3, the anode electrode 5b, which is positioned on the reverse face of the solid polymer electrolyte membrane 5a, is hidden. The part contained by the anode electrode 5b and the cathode electrode 5c in the electricity generating layer 20 serves as a electricity generating surface.

A hydrogen supply path 24 is arranged on the surface of the separator 22 facing toward the anode electrode 5b, as a zigzag shaped channel on the anode side, and the hydrogen supply hole 33 and hydrogen discharge hole 36 of the separator 22 are connected by the hydrogen supply path 24. This hydrogen supply path 24 is located in a region corresponding to the anode electrode 5b (that is, the region corresponding to the generating surface).

Furthermore, an acetone supply path 25 is arranged on the surface of the separator 23 facing toward the cathode electrode 5c, as a zigzag shaped channel on the cathode side, and the acetone supply hole 31 and the acetone discharge hole 34 of the separator 23 are connected by the acetone supply path 25. This acetone supply path 25 is located in a region corresponding to the cathode electrode 5c (that is, the region corresponding to the generating surface).

When the MEA 21 and the separators 22 and 23 are stacked together, the acetone supply holes 31, the IPA supply holes 32, the hydrogen supply holes 33, the acetone discharge holes 34, the hydrogen-acetone discharge holes 35, the hydrogen discharge holes 36, the refrigerant supply holes 37, and the refrigerant discharge holes 38, of the MEA 21 and the separators 22 and 23, are all aligned together to form continuous holes.

Figure 4:
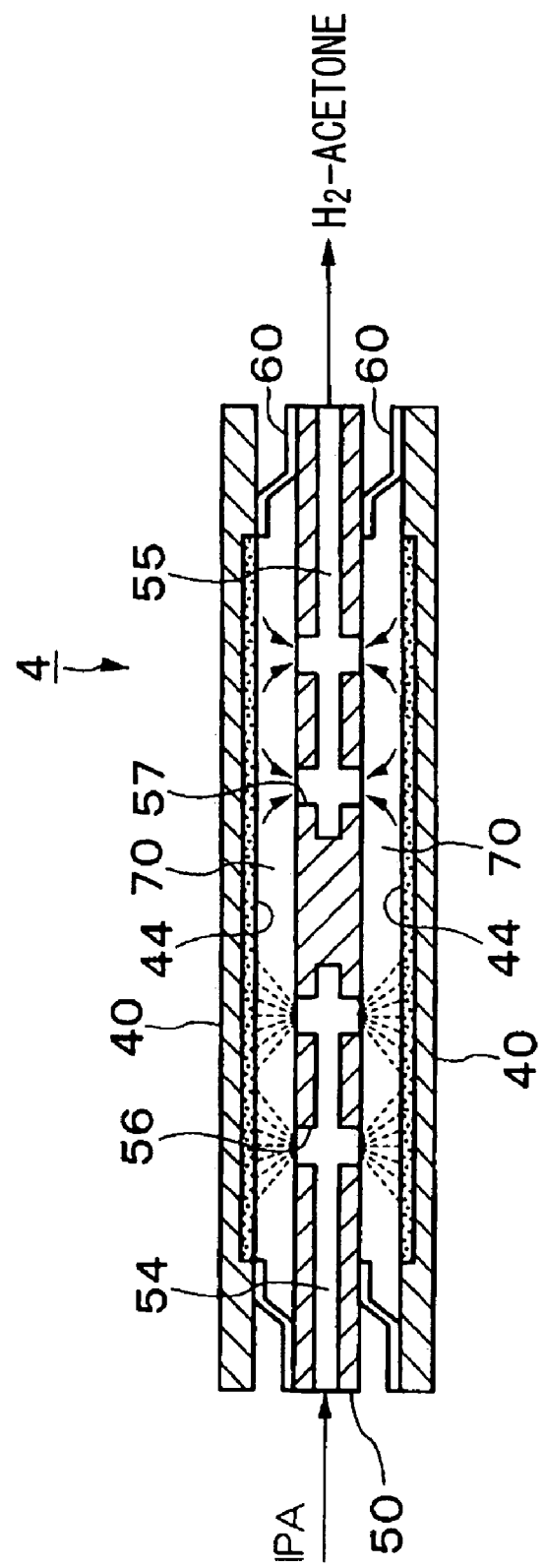
FIG. 4 is a schematic cross-sectional diagram of a module constituting the dehydrogenation reactor in the first embodiment.
Figure 5:
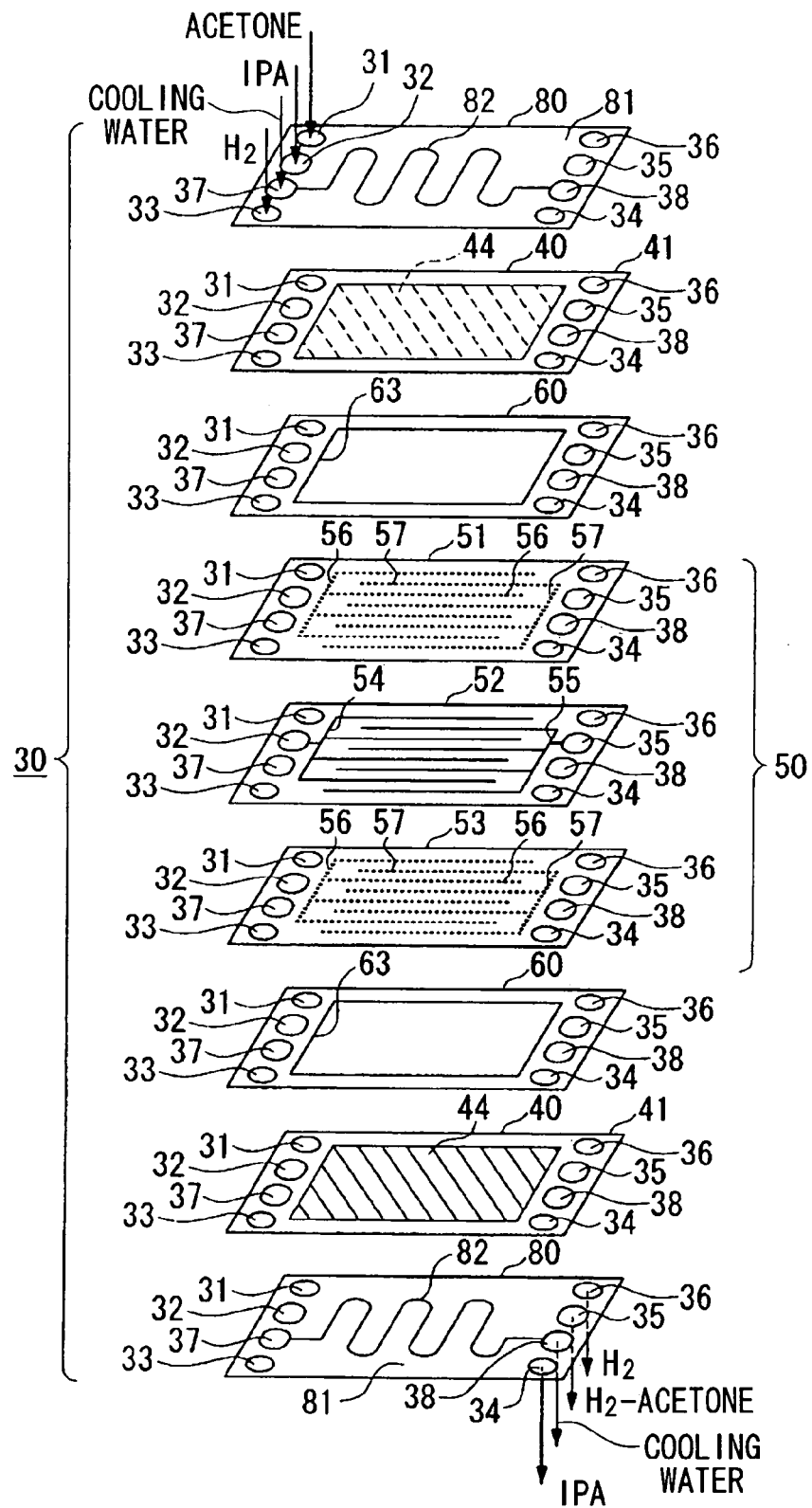
FIG. 5 is an exploded perspective view of the module.

FIG. 4 is a schematic cross-sectional diagram in which a cross section of the module 30 of the dehydrogenation reactor is shown schematically, and FIG. 5 is an exploded perspective view of the module 30. FIG. 4 is a schematic diagram in which part of the structure is omitted, so it does not correspond exactly with FIG. 5.

The module 30 of the dehydrogenation reactor 4 is a flat rectangular shape, and the construction is such that catalyst layers 40 are stacked on both sides of a supply and discharge layer 50, with sealing layers 60 being sandwiched between them, and furthermore, heating layers 80 are stacked outside of the catalyst layers 40. Similarly to the arrangement in the case of the electricity generating layers 20 of the sub fuel cell 5, an acetone supply hole 31, an IPA supply hole 32, a hydrogen supply hole 33, an acetone discharge hole 34, a hydrogen-acetone discharge hole 35, a hydrogen discharge hole 36, a refrigerant supply hole 37, and a refrigerant discharge hole 38, are provided, passing through in the laminated direction.

The catalyst layers 40 are rectangular and flat, and incorporate metal substrates 41 of aluminum, stainless steel, or the like. Catalyst sheets 44 are fitted to regions in the centers of the inner surfaces (in other words, the surfaces facing towards the supply and discharge layer 50) of the substrates 41, which correspond to the anode electrode 5b and the cathode electrode 5c of the electricity generating layer 20 (in other words, regions corresponding to the electricity generating surfaces). The catalyst sheets 44 comprise ruthenium (Ru) as a dehydrogenation catalyst, supported on activated carbon, and they are formed into sheets by using polytetrafluoroethylene resin (abbreviated hereunder as PTFE) as a binder, which is fixed to the substrate 41 with adhesive.

In addition, the acetone supply hole 31, the IPA supply hole 32, the hydrogen supply hole 33, the acetone discharge hole 34, the hydrogen-acetone discharge hole 35, the hydrogen discharge hole 36, the refrigerant supply hole 37, and the refrigerant discharge hole 38 are arranged in areas away from the catalyst sheet 44.

The catalyst layer 40 constructed in this manner is thin, and a large area can be used for the parts where the dehydrogenation catalyst is supported.

The supply and discharge layer 50 is rectangular and flat, and incorporates three metal substrates 51, 52 and 53, of aluminum, stainless steel, or the like. Similarly to the arrangement in the case of the electricity generating layers 20 of the sub fuel cell 5, acetone supply holes 31, IPA supply holes 32, hydrogen supply holes 33, acetone discharge holes 34, hydrogen-acetone discharge holes 35, hydrogen discharge holes 36, refrigerant supply holes 37, and refrigerant discharge holes 38, are provided, passing through the supply and discharge layer 50 in the laminated direction.

In the middle substrate 52, an IPA supply path 54, which passes through from the top surface to the reverse surface of the substrate 52, is arranged in a comb shape, with the IPA supply hole 32 being the start point, and is formed over the whole area corresponding to the catalyst sheets 44 of the catalyst layers 40. Furthermore, in this substrate 52, a hydrogen-acetone discharge path 55, which passes through from the top surface to reverse surface of the substrate 52 is arranged in a comb shape, with the hydrogen-acetone discharge hole 35 being the start point, and is formed over the whole area corresponding to the catalyst sheets 44 of the catalyst layers 40. The IPA supply path 54 and the hydrogen-acetone discharge path 55 are arranged in a form such that the comb teeth parts mesh.

In the substrates 51 and 53 positioned on the two sides of the supply and discharge layer 50, a number of supply holes 56 is arranged at a predetermined spacing along the IPA supply path 54 of the substrate 52, and a number of discharge holes 57 is arranged at a predetermined spacing along the hydrogen-acetone discharge path 55 of the substrate 52. These supply holes 56 and discharge holes 57 are arranged adjacent to each other and distributed over a wide area.

These three substrates 51, 52 and 53 are integrated by joining by an appropriate joining method such as diffusion bonding, soldering, or the like, in a state whereby they make full contact, to form the supply and discharge layer 50. By this joining, the apertures on the face and back of the IPA supply path 54 and hydrogen-acetone discharge path 55 installed in the substrate 52 are sealed by the substrates 51 and 53, and only the supply holes 56 and the discharge holes 57 are left open.

In this manner, since the supply and discharge layer 50 has a stacked structure of three substrates 51, 52 and 53, it can be made thin, and a number of supply holes 56 and discharge hole 57 can be provided. Thus it is possible to obtain a large total aperture area of the supply holes 56 and the discharge holes 57.

Figure 6:
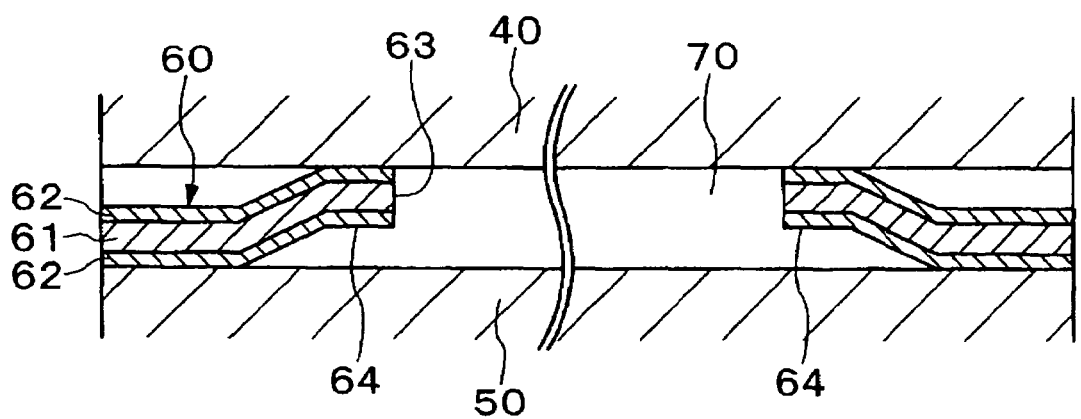
FIG. 6 is a cross-sectional diagram showing an example of sealing layers used for the module.
Figure 7:
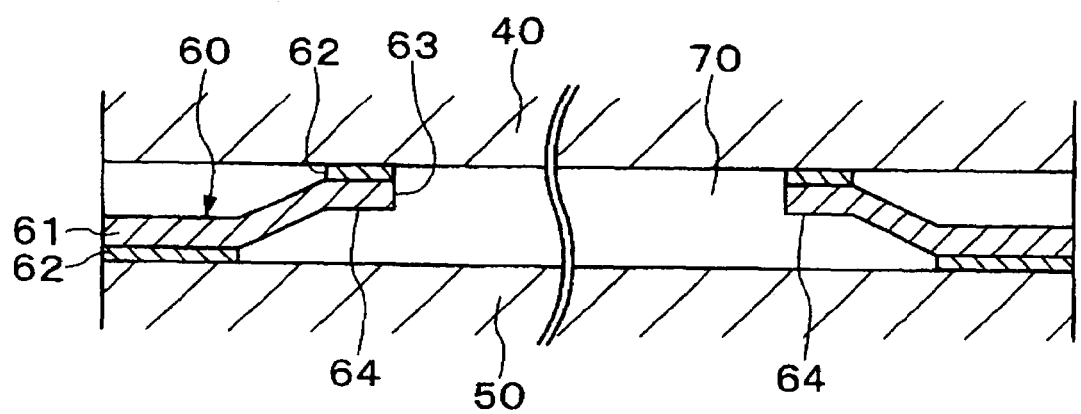
FIG. 7 is a cross-sectional diagram showing another example of sealing layers used for the module.
Figure 8:
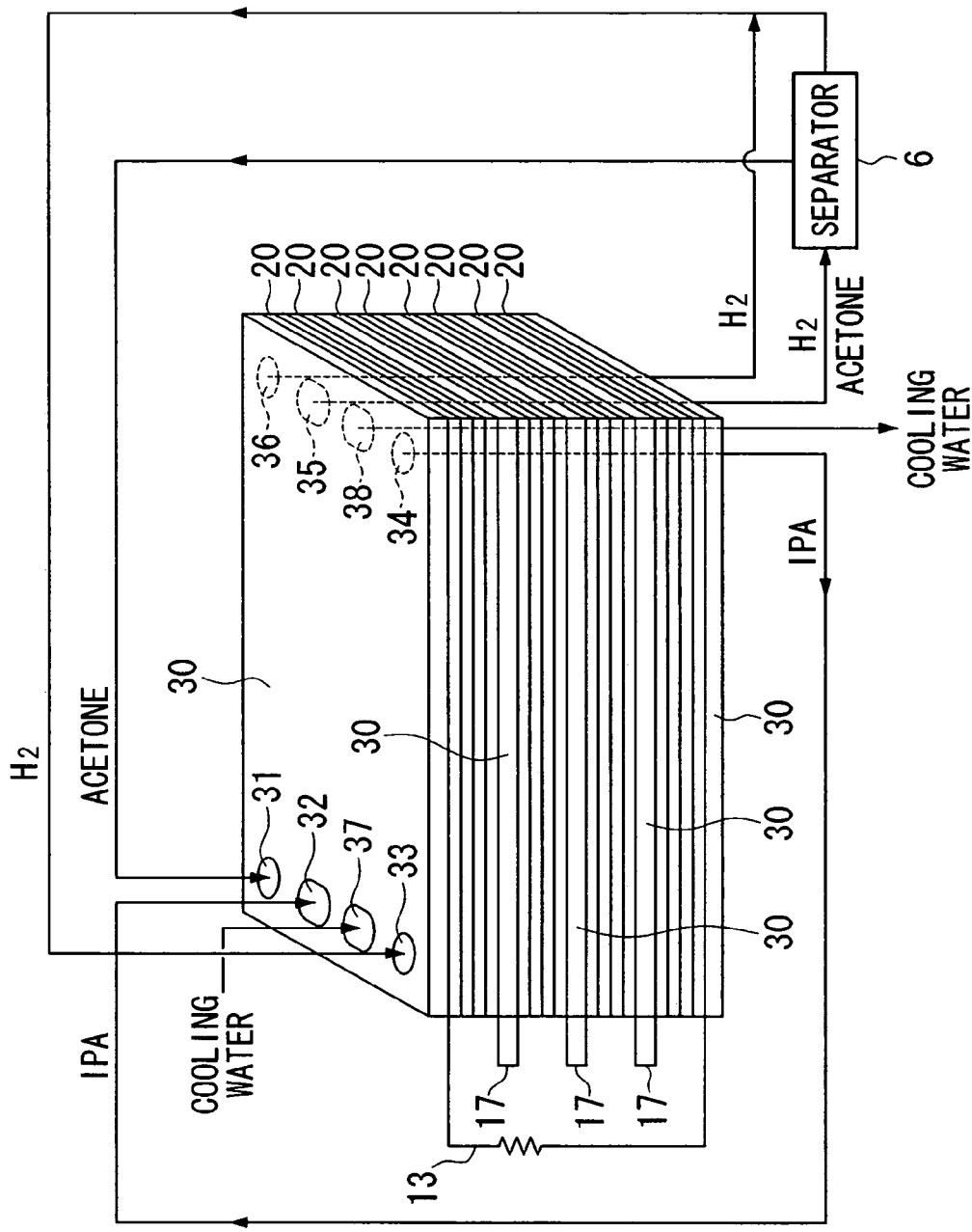
FIG. 8 is a conceptual diagram showing another example of the case where the dehydrogenation reactor and the sub fuel cell in the first embodiment of a thermoelectric conversion apparatus according to the present invention are integrated.

The sealing layers 60, which are sandwiched between the catalyst layers 40 and the supply and discharge layer 50, are rectangular and almost flat, and are constructed by coating PTFE onto the face and back of a metal substrate 61 of stainless steel or the like, as shown in FIG. 6. A PTFE coating 62 can be formed by spraying a coating liquid made of PTFE and calcinating, after the surface of the substrate 61 to be coated is roughened by sand blasting or the like.

Similarly to the arrangement in the case of the electricity generating layers 20 of the sub fuel cell 5, acetone supply holes 31, IPA supply holes 32, hydrogen supply holes 33, acetone discharge holes 34, hydrogen-acetone discharge holes 35, hydrogen discharge holes 36, refrigerant supply holes 37, and refrigerant discharge holes 38, are provided, passing through each sealing layer 60 in the thickness direction.

Furthermore, apertures 63, which open in the region corresponding to the catalyst sheets 44 (in other words, the region corresponding to the generating surface) of the catalyst layers 40, are formed in the sealing layers 60. In each sealing layer 60, the areas surrounding the acetone supply hole 31, the IPA supply hole 32, the hydrogen supply hole 33, the acetone discharge hole 34, the hydrogen-acetone discharge hole 35, the hydrogen discharge hole 36, the refrigerant supply hole 37, the refrigerant discharge hole 38, and the aperture 63 are seals, and beads 64 are formed in these seals as shown in FIG. 6.

The heating layers 80 are also rectangular and flat, and formed from a metal substrate 81 of aluminum, stainless steel or the like. Similarly to the arrangement in the case of the electricity generating layers 20 of the sub fuel cell 5, acetone supply holes 31, IPA supply holes 32, hydrogen supply holes 33, acetone discharge holes 34, hydrogen-acetone discharge holes 35, hydrogen discharge holes 36, refrigerant supply holes 37, and refrigerant discharge holes 38, are provided, passing through the heating layers 80 in the laminated direction.

In each substrate 81 of the heating layers 80, a refrigerant path 82, which passes through the substrate 81 from the top surface to the reverse surface, is provided over the whole area corresponding to the catalyst sheets 44 of the catalyst layers 40 in a zigzag line, and the refrigerant supply hole 37 and refrigerant discharge hole 38 of the substrate 81 are connected by the refrigerant path 82. Refrigerant, which is warmed when passing through the main fuel cell 2, flows through this refrigerant path 82, so that the catalyst layers 40 are heated. Particularly since the refrigerant path 82 is provided in a zigzag line along each catalyst sheet 44, it is possible to heat the catalyst sheets 44 efficiently.

The module 30 of the dehydrogenation reactor 4 is formed by stacking the catalyst layers 40 on both sides of the supply and discharge layer 50 constructed in this manner, with the sealing layers 60 sandwiched between them, and stacking the heating layers 80 outside of the catalyst layers 40, and it is possible to integrate the dehydrogenation reactor 4 and the sub fuel cell 5 by stacking the modules 30 and the electricity generating layers 20 of the sub fuel cell 5 alternately, and fastening them together using straps or bolts, which are not shown in the figure. At this time, by stacking such that the electricity generating layers 20 and the catalyst layers 40 of the dehydrogenation reactor 4 make contact with each other, it is possible to transfer the self-generated heat of the sub fuel cell 5 directly to the catalyst layers 40, so that heat loss can be reduced dramatically. Furthermore, when the sub fuel cell 5 and the dehydrogenation reactor 4 are stacked, the beads 64 of the sealing layers 60 are deformed elastically. Thus it is possible to ensure that the surface pressure in the sealing sections between the sealing layers 60 and the catalyst layers 40, or the supply and discharge layer 50, is a predetermined magnitude. Moreover, when the PTFE coatings 62 of the beads 64 are pressed onto the sealing surface of the catalyst layers 40, or the supply and discharge layer 50, since the PTFE coatings 62 adapt to the minute unevenness of the sealing surfaces, it is possible to realize extremely good sealing.

Furthermore, by stacking in this manner, a reaction chamber 70, which contains a catalyst sheet 44 and is sealed tightly by the sealing layer 60, is formed between each catalyst layer 40 and the supply and discharge layer 50 as shown in FIG. 4 and FIG. 6. In this embodiment, the PTFE coatings 62 are formed over the whole of the front and reverse surfaces of the substrate 61 of the sealing layer 60. However, even if the PTFE coatings 62 are formed on only the sealing surfaces between the beads 64 and the catalyst layers 40, or the supply and discharge layer 50, it is possible to obtain the same functions and effects as above.

Moreover, by stacking in this manner, corresponding acetone supply holes 31, IPA supply holes 32, hydrogen supply holes 33, acetone discharge holes 34, hydrogen-acetone discharge holes 35, hydrogen discharge holes 36, refrigerant supply holes 37, and refrigerant discharge holes 38 of the electricity generating layers 20 and the modules 30 are all connected together to form continuous holes. Here, the ends of each of the continuous holes are closed.

Hydrogen separated by the separator 6 is supplied to the hydrogen supply hole 33 of the sub fuel cell 5, which is integrated with the dehydrogenation reactor 4 in this manner. This hydrogen is supplied from the hydrogen supply hole 33 of each of the electricity generating layers 20 to the anode electrode 5b through the hydrogen supply path 24 of the substrate 22, and unreacted hydrogen is discharged from the hydrogen supply path 24 to the hydrogen discharge hole 36. The unreacted hydrogen discharged to the hydrogen discharge hole 36 of each of the electricity generating layers 20 is returned to the anode side (hydrogen supply hole 33) of the sub fuel cell 5 through the hydrogen circuit 11 as described previously.

Furthermore, acetone, which is separated by the separator 6, is supplied to the acetone supply hole 31 of the sub fuel cell 5 integrated with the dehydrogenation reactor 4. This acetone is supplied from the acetone supply hole 31 of each of the electricity generating layers 20 to the cathode electrode 5c through the acetone supply path 25 of the substrate 23, and IPA produced by the hydrogenation reaction is discharged from the acetone supply path 25 to the acetone discharge hole 34 with the unreacted acetone. Then, the unreacted acetone and the IPA discharged to the acetone discharge hole 34 of each of the electricity generating layers 20 are returned to the IPA tank 8 as described previously.

In the sub fuel cell 5, electrical energy is generated by a hydrogenation reaction of acetone, and heat is generated along with the hydrogenation reaction. This is self-generated heat of the thermoelectric conversion apparatus 100, and this heat is transferred to the substrates 41 of the catalyst layers 40 of the modules 30 in the dehydrogenation reactor 4 via the substrates 22 and 23 of the sub fuel cell 5. Thus the modules 30 are heated directly.

On the other hand, IPA is supplied via the IPA pump 9 to the IPA supply hole 32 of the dehydrogenation reactor 4 with which the sub fuel cell 5 is integrated. This IPA flows from the IPA supply hole 32 of each of the modules 30 to the IPA supply path 54 of the substrate 52, and is ejected from the supply holes 56 of the substrates 51 and 53 to the corresponding reaction chambers 70. As a result, the IPA is supplied to the catalyst sheets 44 of the catalyst layers 40. In particular, in this embodiment, since a number of supply holes 56 is arranged over almost the whole area corresponding to the catalyst sheets 44, it is possible to form a uniform liquid IPA film over almost the whole of the surfaces of the catalyst sheets 44.

Heat generated by the hydrogenation reaction in the electricity generating layers 20 of the sub fuel cell 5 (in other words, self-generated heat) is added to the catalyst sheets 44 as described above, and waste heat from the main fuel cell 2 is also added via the cooling water circulating circuit 3 connecting the refrigerant discharge holes 38 and the refrigerant supply holes 37. As a result, the IPA induces an endothermic dehydrogenation reaction in the dehydrogenation catalyst of the catalyst sheets 44, and hydrogen and acetone are produced. The hydrogen and acetone are in a vapor phase, and are emitted from the EPA as a liquid film. It is possible for the acetone to induce a hydrogenation reaction and return to IPA. However, in this embodiment, since the IPA is in a liquid film in the catalyst sheets 44, it is therefore possible to suppress the abovementioned hydrogenation reaction, and it is possible to obtain a high conversion rate exceeding the equilibrium conversion rate. Here, conversion rate means the mole ratio of the amount of hydrogen produced to the amount of IPA supplied, and equilibrium conversion rate means the equilibrium value of the conversion rate, which is determined thermodynamically at a certain temperature and pressure in a particular closed system.

The hydrogen and acetone produced by the endothermic dehydrogenation reaction in the reaction chamber 70 are discharged to the hydrogen-acetone discharge path 55 of a substrate 52 passing through the discharge holes 57 provided in the substrates 51 and 53 of the supply and discharge layer 50, and further discharged from the hydrogen-acetone discharge path 55 to the hydrogen-acetone discharge hole 35. Especially in this embodiment, since a number of discharge holes 57 is arranged over almost the whole area corresponding to the catalyst sheets 44, it is possible to shorten the travel distance up until the hydrogen and acetone produced flow into the discharge holes 57. Thus it is possible to discharge the hydrogen and acetone from the reaction chamber 70 quickly before the acetone induces a hydrogenation reaction. Then, the hydrogen and acetone discharged to the hydrogen-acetone discharge hole 35 of each of the electricity generating layers 20 are transferred to the separator 6 as described previously.

In this manner, in the module 30 of this dehydrogenation reactor 4, the supply holes 56 and discharge holes 57 are arranged on the same substrate 52 in the supply and discharge layer 50, and the supply of IPA and discharge of hydrogen-acetone are performed through the same substrate 52. Thus it is possible to simplify the structure of the supply and discharge layer 50, and make the supply and discharge layer 50 thin.

Since the module 30 of this dehydrogenation reactor 4 is constructed by stacking the catalyst layers 40, which are thin and have a large area in which the dehydrogenation catalyst is supported, and the supply and discharge layer 50, which is thin and has a large total aperture area for the IPA supply holes 56 and the hydrogen-acetone discharge holes 57, even though it is small, it is possible to increase its performance. Thus it is possible to miniaturize and reduce the thickness of the dehydrogenation reactor 4, and increase its performance. Furthermore, it is possible to change the performance of the dehydrogenation reactor 4 easily by simply increasing or decreasing the number of modules 30.

Especially in this module 30, since the catalyst layers 40 are located on both the front and reverse sides of the supply and discharge layer 50, and the supply of IPA and discharge of hydrogen-acetone are performed on both the front and reverse sides of the supply and discharge layer 50, the effects of miniaturizing and reducing the thickness of the module 30 and the dehydrogenation reactor 4, and the increase in their performance, are great.

Furthermore, since the sealing layer 60 has a structure in which PTFE is coated onto the metal substrate 61, and the beads 64 are formed on the seals, it is possible to reduce the thickness of the sealing layer 60 while maintaining the surface pressure, which also contributes to the miniaturization of the module 30. Moreover, PTFE excels in corrosion resistance against acetone, IPA and the like, and also excels in heat resistance, so it does not deteriorate and break down under the temperature conditions of 80 to 150° C. where dehydrogenation reactions are performed.

For example, if ethylene propylene diene monomer (EPDM) or the like, which is resistant to acetone, is used in the above-described environment, solvent leaks out of the EPDM, poisoning the dehydrogenation catalyst, and becoming mixed into the hydrogen produced, or the like. However, this does not happen with PTFE.

Furthermore, since the flat electricity generating layers 20 constituting the sub fuel cell 5 and the flat modules 30 constituting the dehydrogenation reactor 4 are stacked, it is possible to integrate the sub fuel cell 5 and the dehydrogenation reactor 4 easily, enabling miniaturization. Thus it can easily be loaded into a vehicle, or the like.

Moreover, as described previously, since the thermoelectric conversion apparatus 100 is constructed as a closed circuit containing the dehydrogenation reactor 4 and the sub fuel cell 5, and self-generated heat of the sub fuel cell 5 is supplied to the dehydrogenation reactor 4 to use for the dehydrogenation reaction, the thermoelectric conversion efficiency is high.

Especially in this first embodiment, since the electricity generating layers 20 of the sub fuel cell 5 and the modules 30 of the dehydrogenation reactor 4 are stacked, it is possible to transfer the heat generated by the electricity generating layers 20 to the catalyst layers 40 of the modules 30 directly. Thus it is possible to reduce heat loss dramatically, and increase the fuel heat utilization factor $\eta H$ of the self-generated heat, increasing the dehydrogenation reaction efficiency of the dehydrogenation reactor 4. As a result, it is possible to increase the thermoelectric conversion efficiency $\eta$.

Furthermore, since the heat required for the dehydrogenation reaction is supplied by waste heat from the main fuel cell 2 and the sub fuel cell 5, it is not necessary to prepare a new heat source for the dehydrogenation reaction. Thus it is possible to simplify the system structure, and vehicle fuel consumption is improved by the energy saving.

The modules 30 of the dehydrogenation reactor 4 and the electricity generating layers 20 of the sub fuel cell 5 are not always stacked alternately, and one module 30 of the dehydrogenation reactor 4 may be stacked per a plurality of electricity generating layers 20 of the sub fuel cell 5. Alternatively, the opposite may be used, and one electricity generating layer 20 of the sub fuel cell 5 may be stacked per a plurality of modules 30 of the dehydrogenation reactor 4.

Embodiment 2

Figure 9:
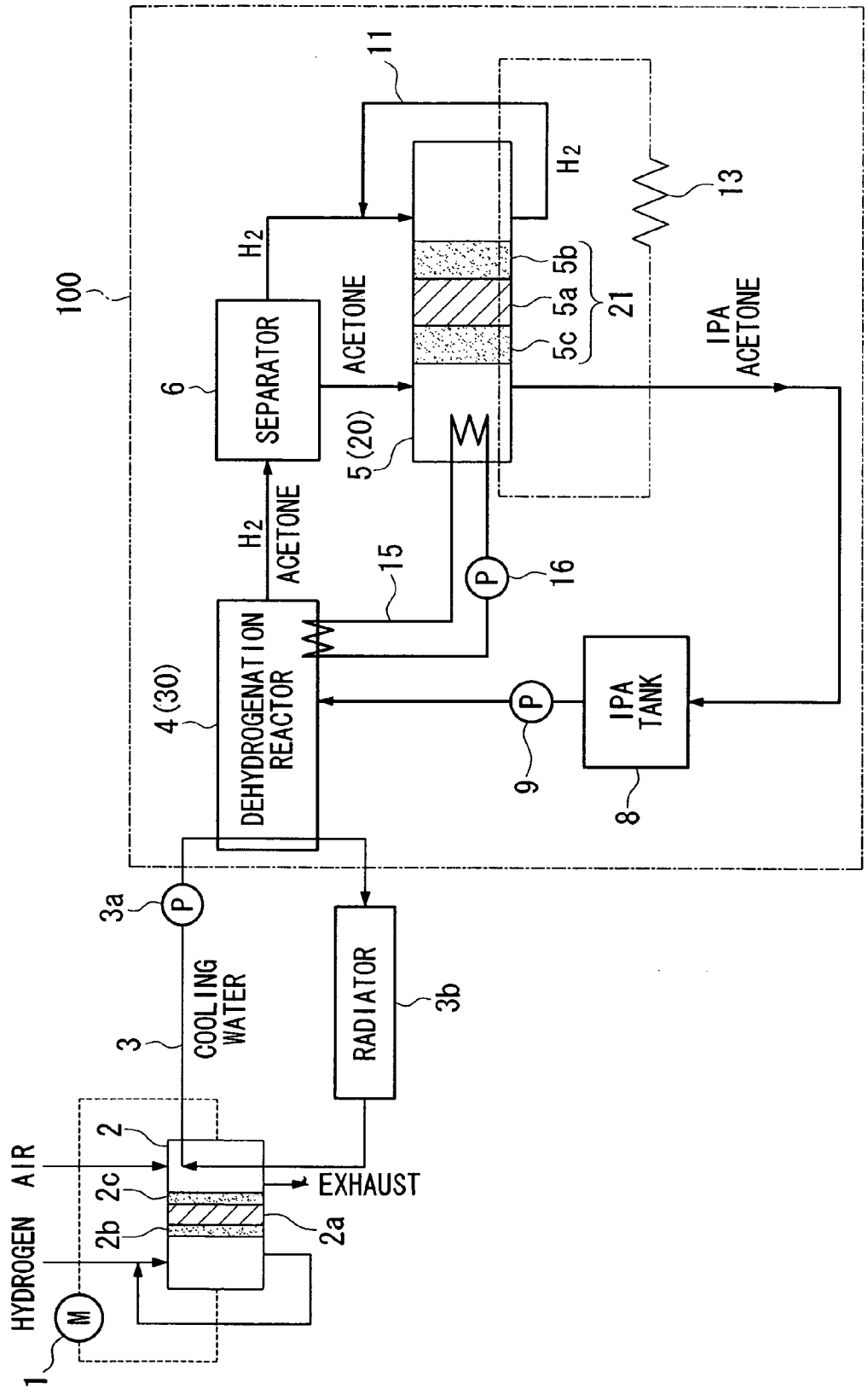
FIG. 9 is a schematic structural diagram of a vehicle fuel cell system incorporating a thermoelectric conversion apparatus of a second embodiment according to the present invention.
Figure 10:
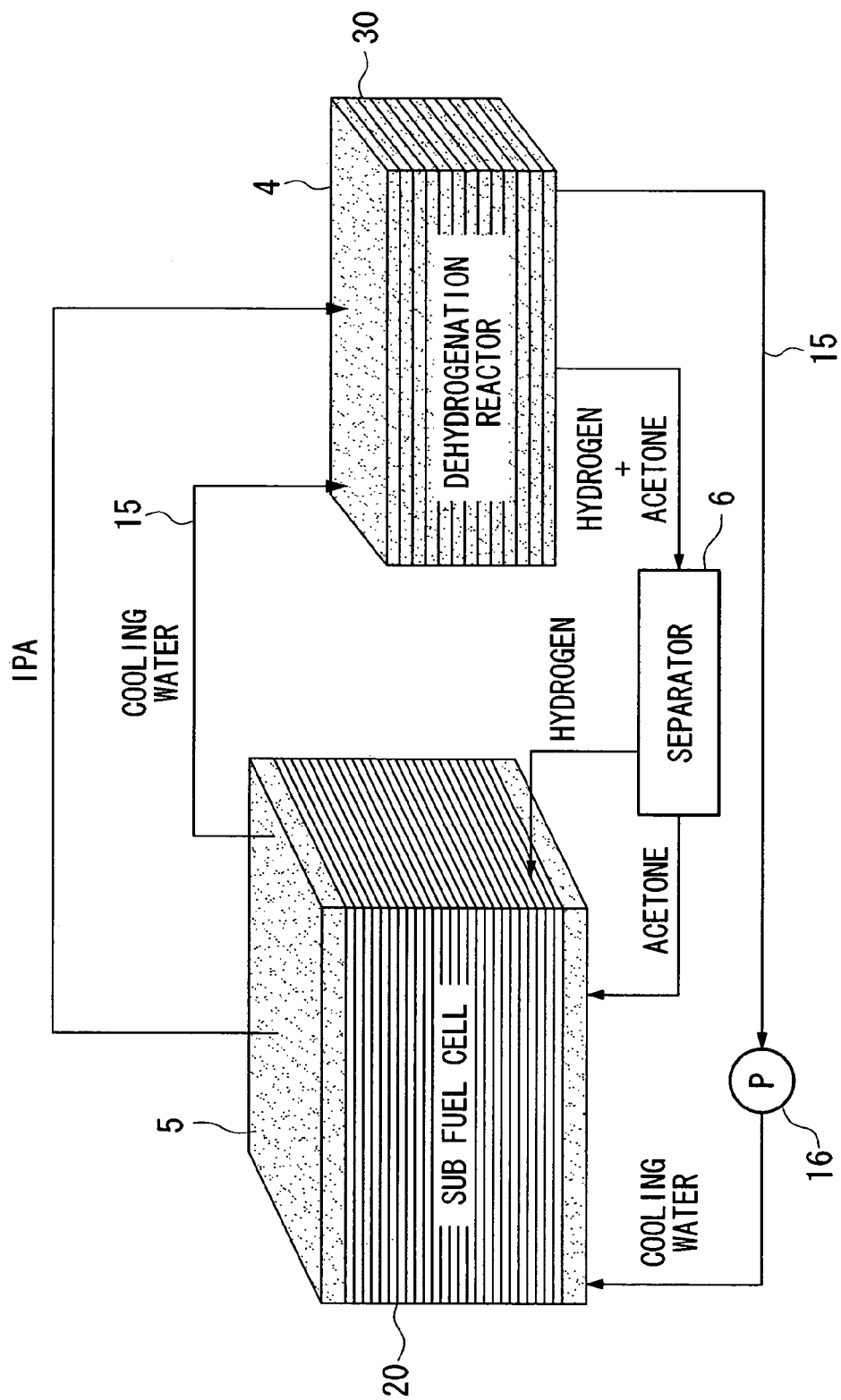
FIG. 10 is a schematic diagram of the thermoelectric conversion apparatus in the second embodiment.

Next is a description of a second embodiment of a thermoelectric conversion apparatus according to the present invention with reference to the drawings of FIG. 9 and FIG. 10.

FIG. 9 is a schematic structural diagram of a vehicle fuel cell system incorporating a thermoelectric conversion apparatus 100 of the second embodiment, and FIG. 10 is a schematic diagram of the thermoelectric conversion apparatus 100.

In the first embodiment described previously, the modules 30 and the electricity generating layers 20 are stacked to integrate the dehydrogenation reactor 4 and the sub fuel cell 5. However, in the second embodiment, the dehydrogenation reactor 4 and sub fuel cell 5 are separate entities. The dehydrogenation reactor 4 is constructed by stacking only the modules 30, and the sub fuel cell 5 is constructed by stacking only the electricity generating layers 20. Then, the dehydrogenation reactor 4 and the sub fuel cell 5 are connected by a cooling water circulating circuit (a heating medium circulating path) 15, and self-generated heat from the sub fuel cell 5 is transferred to the dehydrogenation reactor 4 via cooling water.

In this case, it is desirable to control the flow rate of the cooling water by a cooling water pump 16 such that the temperature of the sub fuel cell 5 is at a predetermined temperature.

The structures of the other parts are the same as in the first embodiment, so the same reference symbols are used for the same parts, and the descriptions are omitted.

It is also possible to supply self-generated heat from the sub fuel cell 5 to the dehydrogenation reactor 4 to utilize it for a dehydrogenation reaction by using the thermoelectric conversion apparatus 100 of this second embodiment. Therefore, it is possible to increase the thermoelectric conversion efficiency similarly to the case of the first embodiment.

Furthermore, in this second embodiment, since the dehydrogenation reactor 4 and the sub fuel cell 5 are separate entities, it is possible to increase the flexibility in the shape and size of the thermoelectric conversion apparatus 100, and the flexibility in its layout, and to control the temperatures of the fuel cell and the dehydrogenation reactor individually by cooling water. For example, in the case where the temperature of the cooling water is increased by the electric power generation of the main fuel cell 2 such that the temperature of the cooling water is higher than normal, it may flow through a bypass, which is not shown in the figure, so as to bypass the dehydrogenation reactor 4. Furthermore, it is also possible to increase the amount of dehydrogenation by increasing the amount of IPA supplied to the dehydrogenation reactor 4.

Other Embodiments

This invention is not limited to the embodiments described above.

For example, in the dehydrogenation reactor 4 of the above-described embodiments, IPA is supplied from one supply and discharge layer 50 to two catalyst layers 40 located on both the front and reverse sides thereof, and hydrogen-acetone produced by the two catalyst layers 40 is discharged to the one supply and exhaust layer 50. However, the supply of IPA and the discharge of hydrogen-acetone may be performed between one supply and discharge layer 50 and one catalyst layer 40 located on just one of the front and reverse sides thereof.

Furthermore, the organic compound to be dehydrogenated is not limited to IPA, and it is possible to use any of the family of decalin, 2-propanol, cyclohexanol, cyclohexane, methylcyclohexane, dimethylcyclohexane, or the like.

Moreover, the dehydrogenated substance is not limited to acetone, but is determined by the organic compound used. It is possible to use any of the family of naphthalene, cyclohexane, benzene, toluene, xylene or the like, other than acetone.

Furthermore, the organic compound is supplied to the catalyst layers 40 so as to form a liquid film. However, it is not limited to a liquid film state.

Moreover, the construction is such that heat from the main fuel cell 2 is transferred to the dehydrogenation reactor 4 as a heat source. However, it is not limited to waste heat of the main fuel cell 2, and conventionally exhausted excess heat may also be used, for example waste heat from the cooling water of an internal combustion engine.

As described above, according to the first aspect of the invention, an effect is demonstrated whereby it is possible to increase the thermoelectric conversion efficiency of a thermoelectric conversion apparatus.

According to the second aspect of the invention, it is possible to transfer heat generated in a fuel cell directly to a dehydrogenation reactor, and it is possible to reduce heat loss dramatically. Thus, the fuel heat utilization factor of self-generated heat is increased. As a result, it is possible to increase the thermoelectric conversion efficiency.

According to the third aspect of the invention, since it is possible to construct a dehydrogenation reactor by simply stacking catalyst layers, and furthermore a supply and discharge layer and an electricity generating layer of the fuel cell are arranged so as to be in contact with the catalyst layers, it is possible to further increase the fuel heat utilization factor of the self-generated heat of the fuel cell, and it is possible to increase the dehydrogenation reaction efficiency of the dehydrogenation reaction. Therefore, it is possible to construct a physically small, but high performance thermoelectric conversion apparatus.

According to the fourth aspect of the invention, since it is possible to further increase the fuel heat utilization factor of the self-generated heat of the fuel cell, it is possible to make the thermoelectric conversion apparatus smaller.

According to the fifth aspect of the invention, it is possible to transfer heat from both surfaces of the supply and discharge layer to the catalyst layers, thus enabling a thermoelectric conversion apparatus with high performance to be made smaller and thinner.

According to the sixth aspect of the invention, since the heat transfer properties of the self-generated heat of the electricity generating layer are improved, the thermoelectric conversion efficiency of the thermoelectric conversion apparatus is further improved.

According to the seventh aspect of the invention, it is possible to increase the thermoelectric conversion efficiency of the thermoelectric conversion apparatus considerably. Furthermore, since it is possible to make the dehydrogenation reactor and the fuel cell different entities, the flexibility in the shape and size of the thermoelectric conversion apparatus, and the flexibility in its layout, are increased, and it is possible to control the temperatures of the fuel cell and the dehydrogenation reactor individually using the heating medium.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description but is only limited by the scope of the appended claims.

What is claimed is:

1. A thermoelectric conversion apparatus comprising:
a dehydrogenation reactor for generating hydrogen and a dehydrogenated substance by an endothermic dehydrogenation reaction of an organic compound in the presence of a dehydrogenation catalyst and heat from a heat source; and
a fuel cell which generates electricity by an electrochemical reaction of said hydrogen and said dehydrogenated substance produced by said dehydrogenation reactor,
wherein the dehydrogenation reactor and the fuel cell are integrated into a stack,
wherein said dehydrogenation reactor is constructed by stacking catalyst layers containing said dehydrogenation catalyst, and supply and discharge layers comprising a supply path for supplying an organic compound to said catalyst layers and a discharge path for discharging hydrogen and the dehydrogenated substance produced in said catalyst layers,
wherein an electricity generating layer of said fuel cell is arranged in contact with said catalyst layer,
wherein said hydrogenation catalyst and the electricity generating surface of said electricity generating layer are arranged so as to contact with each other when stacked, and
wherein said catalyst layers are stacked on both sides of said supply and discharge layer, and an organic compound, hydrogen and a dehydrogenated substance are supplied and discharged between said supply and discharge layer and said catalyst layer on both sides.

2. A thermoelectric conversion apparatus comprising:
a dehydrogenation reactor for generating hydrogen and a dehydrogenated substance by an endothermic dehydrogenation reaction of an organic compound in the presence of a dehydrogenation catalyst and heat from a heat source; and
a fuel cell which electricity by an electrochemical reaction of said hydrogen and said dehydrogenated substance produced by said dehydrogenation reactor,
wherein the dehydrogenation reactor and the fuel cell are integrated into a stack,
wherein said dehydrogenation reactor is constructed by stacking catalyst layers containing said dehydrogenation catalyst, and supply and discharge layers comprising a supply path for supplying an organic compound to said catalyst layers and a discharge path for discharging hydrogen and the dehydrogenated substance produced in said catalyst layers, wherein an electricity generating layer of said fuel cell is arranged in contact with said catalyst layer, and
wherein said catalyst layers are stacked on both sides of said supply and discharge layer, and an organic compound, hydrogen and a dehydrogenated substance are supplied and discharged between said supply and discharge layer and said catalyst layer stacked on both sides of the supply and discharge layer.

3. A thermoelectric conversion apparatus according to claim 2, wherein said catalyst layer and said electricity generating layer are each formed from a metal substrate.

* * * * *